US00PP29874P3

(12) United States Plant Patent
Austin

(10) Patent No.: US PP29,874 P3
(45) Date of Patent: Nov. 27, 2018

(54) ***ROSA HYBRIDA* SHRUB NAMED 'AUSOBLIGE'**

(50) Latin Name: *Rosa hybrida*
Varietal Denomination: AUSoblige

(71) Applicant: David Austin Roses Ltd., Albrighton, Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 15/731,139

(22) Filed: Apr. 24, 2017

(65) Prior Publication Data

US 2018/0098469 P1 Apr. 5, 2018

(30) Foreign Application Priority Data

Sep. 30, 2016 (QZ) ..... PBR 2016/2384

(51) Int. Cl.
*A01H 5/02* (2018.01)
*A01H 6/74* (2018.01)

(52) U.S. Cl.
USPC ..... Plt./103
CPC ..... *A01H 5/02* (2013.01); *A01H 5/0222* (2013.01); *A01H 6/749* (2018.05)

(58) Field of Classification Search
USPC ..... Plt./103
See application file for complete search history.

*Primary Examiner* — Anne Marie Grunberg
(74) *Attorney, Agent, or Firm* — KPPB LLP

(57) ABSTRACT

A variety of rose plant of the shrub class named 'AUSoblige'. The 'AUSoblige' is a variety of a rose with blooms that are suitable for cut-flower production. The flowers are of a white/cream color, with large blooms with around 60 petals, and having leathery, matt green leaves.

1 Drawing Sheet

Classification: The present invention relates to a new *Rosa hybrida* shrub of the market class 'English Rose'.

Variety denomination: The new plant has the varietal denomination 'AUSoblige'.

CROSS-REFERENCE TO RELATED APPLICATION

The present application claims priority to European CPVO 2016/2384, filed Sep. 30, 2016.

ORIGIN OF INVENTION

This invention relates to a new and distinct variety of rose plant suitable for cut-flower production named 'AUSoblige', which was originated from the cross-pollination of the two 'unnamed' and unpatented seedlings of *Rosa hybrida*.

BACKGROUND OF THE INVENTION

The primary objective of this breeding was to produce a rose variety suitable for cut-flower production with large white/creamy double blooms with around 60 petals forming a loose ruffled rosette shaped bloom.

SUMMARY OF THE INVENTION

Among the features which distinguish the new variety from others presently available and commercial rose cultivars known to the inventor is the following combination of characteristics: white/creamy blooms; with around 60 petals; and leathery, matt green leaves.

Asexual reproduction of the new variety by budding as performed at Bowling Green Lane in Albrighton, Britain shows that the foregoing and other distinguishing characteristics come true to form and are established and transmitted through succeeding asexual propagations. 'AUSoblige' may be asexually propagated by budding. The budding successfully occurred on the plant/rootstock *Rosa inermis* for the observed plants.

COMPARISON WITH PARENTS

The maternal and paternal parents of 'AUSoblige' are two unnamed seedlings. The new rose may be distinguished from its maternal parent, by the following combination of characteristics: the maternal parent has a pink coloring and fewer petals. The new rose may be distinguished from its pollen parent, by the following combination of characteristics: the paternal parent also has a pink color.

COMPARISON WITH THE CLOSEST COMMERCIALLY AVAILABLE CULTIVAR

The closest commercially available cultivars to the new variety are the 'AUSpastor' (U.S. Plant Pat. No. 19,254). The new rose may be distinguished from the 'AUSpastor' by the size of the blooms, which are smaller (~8-9 cm), and have many more petals (~160).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

Observations of budded 'AUSoblige' specimens were made at the nursery at David Austin Roses Limited in Albrighton, Wolverhampton, United Kingdom. The following description is of 5 year-old rose plants of the new variety grown in a garden environment in Albrighton, Britain in the month of May. Phenotypic expression may vary with environmental, cultural and climatic conditions, as well as differences in conditions of light and soil.

FLOWER CHARACTERISTICS

Blooming habit: Continuous. The number of blooms per plant during the growing season is profuse, but there are too many to count.

Bud:

*Size*.—About 2 cm long and 1.8 cm in diameter when the petals start to unfurl.

*Form*.—The bud form is pointed ovoid.

*Color*.—When sepals first divide, the bud color is RHS 1C (green yellow group). When half blown, the upper sides of the petals are RHS 1B (green-yellow group), and the lower sides of the petals RHS 155B (green-yellow group).

*Calyx*.—Shape: opens to a star shape, with the sepals finally folding back against the stems. Length: 7.0 cm. Diameter: 7.0 cm.

*Sepals*.—Arrangement: Regularly arranged. Color: Upper Surface: RHS 138B (green group). Lower Surface: RHS 143A (yellow-green group). Length: 3 cm. Width: 1 cm. Shape: Lanceolate. Surface texture: Upper Surface: Downy. Lower Surface: Smooth. Number: There are 3 normally appendaged sepals, and 2 unappendaged sepals with hairy edges.

*Receptacles*.—Color: RHS 143A (green group). Shape: Funnel. Size: Small, about 9 mm long×9 mm wide. Surface: Smooth.

*Peduncle*.—Length: Medium, averaging about 15-30 cm. Surface: Smooth (with occasional prickles). Color: RHS 143A (green group) with RHS 181B (greyed-red group). Strength: Normal.

Blooms:

*Size*.—Large, average open diameter is about 11 cm.

*Borne*.—Several together in the natural state.

*Stems*.—Strength: Normal, average length is about 75 cm. Diameter: 5-6 mm.

*Form*.—When first open, bloom is cupped. Permanence of bloom: outer petals curl back.

Petalage: Number of petals under normal conditions: 60.

*Color*.—The upper sides of the petals are RHS 155C (white group). The reverse sides of the petals are RHS 155C (white group). The base of the petals has a yellow spot that is RHS 2D (yellow group)

*Variegations*.—None.

*Discoloration*.—The general tonality at the end of the first day is RHS 155C (white group), and at the end of the third day is RHS 155C (white group).

*Fragrance*.—Moderate. Character of fragrance: Musk.

Petals:

*Texture*.—Smooth.

*Size*.—Width: 30-40 mm. Length: 45 mm.

*Surface*.—Smooth.

*Shape*.—Obovate.

*Margin*.—Mostly entire, with some having incisions.

*Apex shape*.—Rounded.

*Base shape*.—Cuspidate.

*Form*.—Slightly incurved.

*Arrangement*.—Informal.

*Petaloids*.—Number: Around 10-12. Color: RHS 155C (white group). Length: 1.5-2.5 cm. Width: 1 cm. Shape: Obovate. Margin: Entire.

*Persistence*.—Petals hang on and dry.

*Lastingness*.—On the plant: not tested. As a cut flower: about 11 days.

Reproductive parts:

*Stamens*.—Number: 4-6. Length: 1 cm.

*Anthers*.—Length: 2-2.5 mm. Color: RHS 22A (yellow-orange group). Arrangement: Regular around styles with some mixed with petaloids.

*Filaments*.—Color: RHS 154C (yellow-green group). Length: 9 mm.

*Pollen*.—Color: RHS 22A (yellow-orange group). Amount: Moderate

*Pistils*.—Number: 40. Length: 10-15 mm.

*Styles*.—Color: RHS 157A (green-white group). Length: 8-14 mm.

*Stigmas*.—Color: RHS 157A (green-white group). Length: 1-1.5 mm.

*Hips*.—NONE Observed.

PLANT CHARACTERISTICS

Plant form: Shrub.

Plant growth: Medium.

Age to maturity: 1 years.

Mature plant: Height: 1 m. Width: 50 cm.

Rootstock: *Rosa inermis* for the observed plants in the UK.

Foliage:

*Number*.—Leaflets on normal mid-stem leaves is: 5 (including terminal leaflet).

*Size*.—Large, about 17 cm long×15 cm wide.

*Quantity*.—Normal. Number of leaves per flowering stem is: 10.

*Color*.—New foliage: Upper side: RHS 146A (yellow-green group) tinged with RHS 183B (greyed-purple group). Lower side: RHS 183B (greyed-purple group). Old foliage: Upper side: RHS 137A (green group). Lower side: RHS 138A (green group).

Leaflets:

*Size*.—About 7 cm long×5 cm wide.

*Shape*.—Pointed oval.

*Base shape*.—Cordate.

*Apex shape*.—Acuminate.

*Texture*.—Leathery.

*Edge*.—Serrated.

*Serrations*.—Single and large.

*Petiole*.—Color: RHS 143C (green group). Length: 5 cm. Width: 2 mm. Surface Texture: Glandular.

*Petiole rachis*.—Color: RHS 143C (green group). Underside: with prickles.

*Stipules*.—Length: 2.5 cm, glandular. Color: RHS 143C (green group).

*Auricle*.—Shape: Lanceolate. Length: 8 mm. Width: 2 mm. Color: RHS 143C (green group).

*Vein color*.—Color: Same as leaf color.

*Venation pattern*.—Reticulate.

Wood:

*New wood*.—Color: RHS 143C (green group). Bark: Smooth.

*Old wood*.—Color: RHS 143C (green group). Bark: Smooth.

Branching habit:

*Number*.—0.

Stems:

*Mature stem*.—Length: 75 cm. Diameter: 7 mm.

*Internode distance*.—8-9 cm. The above measurements are all variable, depending on growing conditions in a season.

*Stem pubescence present*.—No.

Prickles:

*Quantity*.—On main canes from base: Few. Number per stem length: 8 per 20 cm. On laterals from main canes: N/A.

*Form*.—Deep concave.

*Length*.—5 mm.

*Color when young*.—RHS 183B (greyed-red group).

*Color when mature*.—RHS 183A (greyed-red group).

Small prickles:

*Quantity*.—Main stalk: None Laterals: None.

Disease resistance:

*Powdery mildew*.—Resistant.

*Downy mildew*.—Resistant.

*Blackspot*.—Resistant.

*Rust*.—Resistant.

Pest resistance: Not tested.

Winter hardiness: Not tested.

Growing conditions: Normal greenhouse conditions.

What is claimed is:

1. A new and distinct variety of rose plant of the shrub class, substantially as herein shown and described.

* * * * *

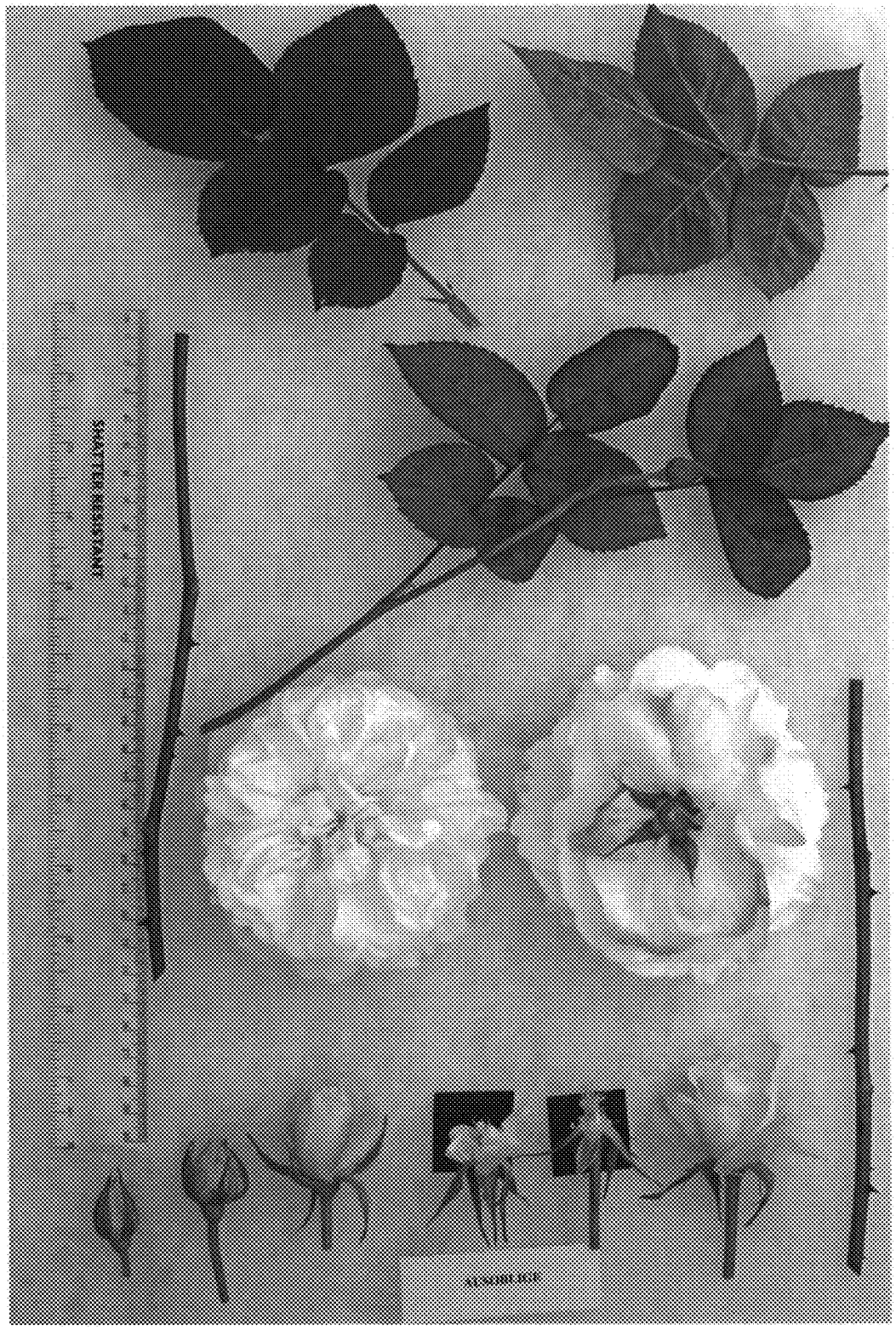
SUITTER RESEARCH
AUGUST